(12) United States Patent
Viguie et al.

(10) Patent No.: US 8,603,343 B2
(45) Date of Patent: Dec. 10, 2013

(54) DEVICE FOR SEPARATING A FINELY DIVIDED SOLID IN SUSPENSION IN A VISCOUS LIQUID

(75) Inventors: Jean Christophe Viguie, Lyons (FR); Willi Nastoll, Lyons (FR); Francois Hugues, Vernaison (FR); Elsa Mignone, Monza (IT); Giuseppe Belmonte, S. Giullano Milanese (IT)

(73) Assignees: IFP Energies Nouvelles, Rueil-Malmaison Cedex (FR); Eni S.p.A., Rome (IT)

( * ) Notice: Subject to any disclaimer, the term of this patent is extended or adjusted under 35 U.S.C. 154(b) by 598 days.

(21) Appl. No.: 12/738,356

(22) PCT Filed: Sep. 18, 2008

(86) PCT No.: PCT/FR2008/001305
§ 371 (c)(1),
(2), (4) Date: Dec. 2, 2010

(87) PCT Pub. No.: WO2009/074731
PCT Pub. Date: Jun. 18, 2009

(65) Prior Publication Data
US 2011/0114541 A1    May 19, 2011

(30) Foreign Application Priority Data
Oct. 18, 2007   (FR) ...................................... 07 07291

(51) Int. Cl.
*B01D 21/24* (2006.01)
*C07C 27/26* (2006.01)
*B01D 21/00* (2006.01)
*C07C 1/04* (2006.01)
*B01D 21/34* (2006.01)

(52) U.S. Cl.
CPC ............ *B01D 21/2405* (2013.01); *B01D 21/34* (2013.01); *B01D 21/0042* (2013.01); *B01D 21/2427* (2013.01); *C07C 1/0485* (2013.01)
USPC ........... 210/744; 210/801; 210/104; 210/519; 210/521; 210/532.1; 210/534; 518/705

(58) Field of Classification Search
USPC .............. 210/800, 801, 519, 521, 532.1, 534, 210/535, 540, 744, 104; 518/705
See application file for complete search history.

(56) References Cited

U.S. PATENT DOCUMENTS

| | | | | |
|---|---|---|---|---|
| 196,259 | A | * | 10/1877 | Solvay ........................ 210/534 |
| 2,593,036 | A | | 4/1952 | Koch |
| 4,132,652 | A | * | 1/1979 | Anderson et al. ............. 210/536 |

(Continued)

FOREIGN PATENT DOCUMENTS

| | | |
|---|---|---|
| DE | 2 209 349 A1 | 9/1973 |
| DE | 44 32 280 A1 | 3/1996 |

(Continued)

OTHER PUBLICATIONS

International Search Report of PCT/FR2008/001305 (Jun. 15, 2009).

*Primary Examiner* — Christopher Upton
(74) *Attorney, Agent, or Firm* — Millen, White, Zelano & Branigan, P.C.

(57) ABSTRACT

The device described in the present invention can separate fine solid particles in suspension in a viscous liquid, withdrawing a clear liquid from the top of the device, and a dense liquid charged with solid particles is withdrawn from the bottom. The invention also concerns the application of this device to the separation of catalyst particles in a liquid phase Fischer-Tropsch synthesis process.

16 Claims, 1 Drawing Sheet

(56) References Cited

U.S. PATENT DOCUMENTS

| | | | |
|---|---|---|---|
| 4,802,978 A * | 2/1989 | Schmit et al. | 210/519 |
| 5,252,205 A * | 10/1993 | Schaller | 210/540 |
| 5,453,197 A * | 9/1995 | Strefling | 210/519 |
| 6,833,078 B2 | 12/2004 | Espinoza et al. | |
| 6,929,754 B2 | 8/2005 | Espinoza et al. | |
| 6,953,123 B2 * | 10/2005 | Niitti | 210/519 |
| 7,078,439 B2 | 7/2006 | Odueyungbo et al. | |
| 7,287,651 B2 * | 10/2007 | Myers et al. | 210/519 |
| 7,360,657 B2 | 4/2008 | Oder et al. | |
| 2007/0056912 A1 | 3/2007 | Oder et al. | |
| 2010/0200511 A1 | 8/2010 | Oder et al. | |

FOREIGN PATENT DOCUMENTS

| | | |
|---|---|---|
| FR | 2 802 828 A1 | 6/2001 |
| GB | 170225 A | 10/1921 |
| WO | WO 01/34266 A1 | 5/2001 |
| WO | WO-2005-035131 A1 | 4/2005 |

* cited by examiner

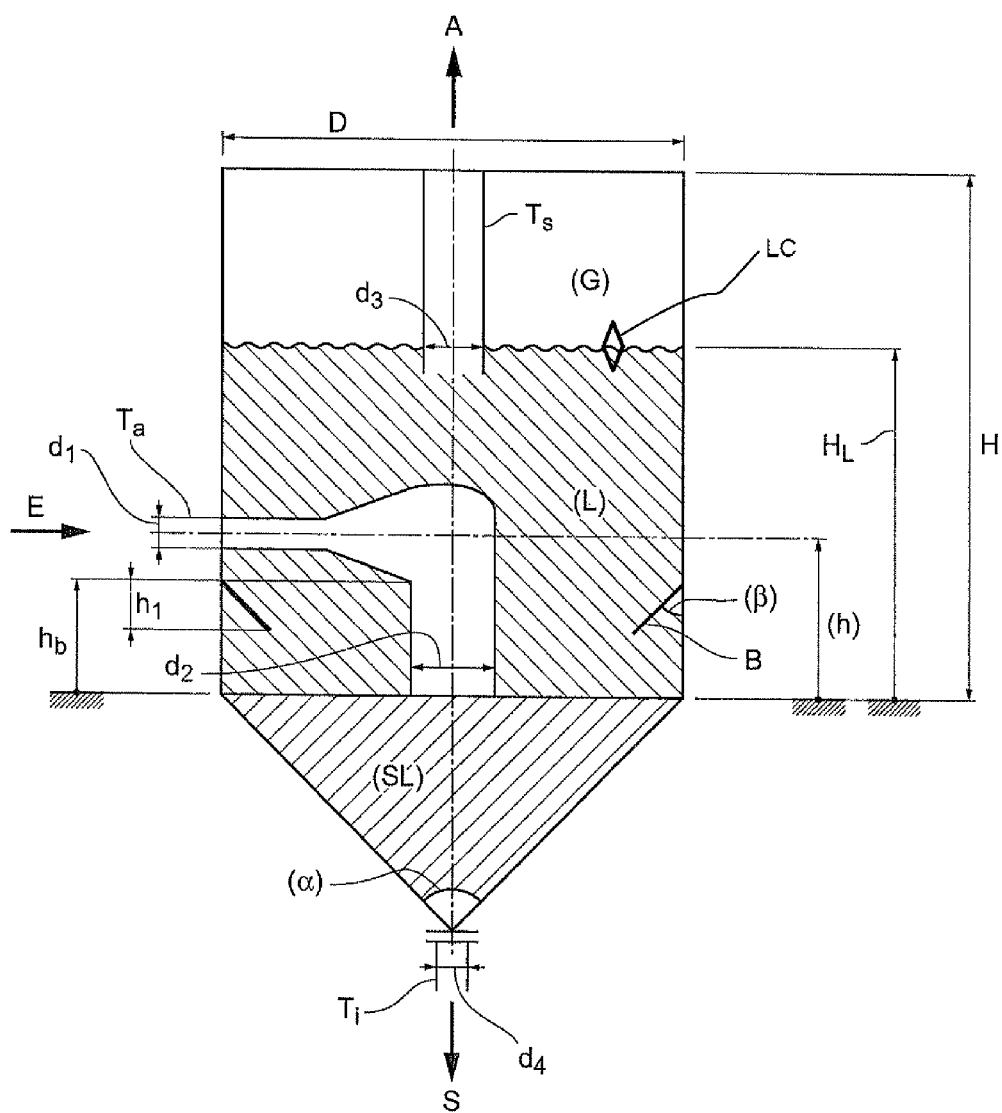

DEVICE FOR SEPARATING A FINELY DIVIDED SOLID IN SUSPENSION IN A VISCOUS LIQUID

FIELD OF THE INVENTION

The present invention falls within the field of devices which can separate, under gravity, fine solid particles contained in a liquid which is viscous to a greater or lesser degree. Said devices are generally known as decanters. They can recover at the top a liquid which is substantially free of particles and a liquid which is concentrated in said particles is recovered from the bottom. In the remainder of the text, we shall use the term "clear liquid" to designate the liquid extracted from the top of the device, and "dense liquid" to designate the liquid which is concentrated in solid particles withdrawn from the bottom of said device.

Decanters are mainly encountered in the sludge treatment and refinery industries for the treatment of water charged with oil.

More particularly, the device of the present invention is adapted to decanting solid particles which have a size in the range 10 to 100 microns (1 micron=1 μm=$10^{-6}$ meter) and with a (particle) density in the range 500 kg/m$^3$ to 2500 kg/m$^3$.

These particles may be fine particles of catalyst, such as those used in a Fischer-Tropsch synthesis reactor operating in the liquid phase with a catalyst in suspension (termed a "slurry reactor" or "slurry"). In this case, the catalyst particles have a diameter in the range 20 to 80 microns, a density in the range 1000 to 2500 kg/m$^3$ and the liquid medium in which they are dispersed has a viscosity in the range 0.2 to 2 mPa·s, preferably in the range 0.5 to 1 mPa·s, and a density in the range 500 to 1000 kg/m$^3$.

The unit of viscosity used throughout the text is the milliPascal·second, i.e. $10^{-3}$ Pascal·s, which is equal to 1 centipoise.

In the remainder of the text, we shall use the term "slurry" to designate a suspension of fine particles dispersed in a liquid medium, the liquid medium itself being traversed by gas bubbles.

EXAMINATION OF THE PRIOR ART

The dimensioning of decanters reposes essentially on the notion of the rate of sedimentation defined as the rate of fall of particles in the liquid under consideration under the effect of gravity alone. Since this rate drops as the particles become smaller and their density falls, decanters are generally very tall to allow fine particles to migrate towards the bottom of the device where they are generally recovered. The decanters generally have large diameters in order to obtain a low linear velocity of flow between the inlet and the outlet of the device, in order to disturb the fall of the particles in the medium under consideration as little as possible.

We shall examine below the prior art in the field of the Fischer-Tropsch process as this constitutes the most frequent application of the present device.

The Fischer-Tropsch process is a process for synthesising hydrocarbon molecules from approximately $C_1$ to $C_{80}$, from a reaction gas termed synthesis gas, essentially constituted by hydrogen ($H_2$) and carbon monoxide (CO), and also carbon dioxide ($CO_2$).

One implementation of this process consists of using fine particles of catalyst based on iron or cobalt, which may or may not be supported, and to bring them into contact with the reaction medium constituted by a gas-liquid mixture, sometimes termed a bubble column.

Particles with diameters in the range 10 to 100 microns, usually in the range 20 to 80 microns, are dispersed in the liquid phase which itself is traversed by gas bubbles, the medium as a whole generally being termed a "slurry".

A "slurry" Fischer-Tropsch process generally comprises a first device which can separate the major portion of the gas from the liquid in which the catalyst particles are dispersed. The gas which is liberated is essentially constituted by light $C_1$ to $C_5$ hydrocarbons, steam formed during the reaction and a greater or lesser fraction of unreacted synthesis gas.

A second separation means located downstream of the first means can separate the particles of catalyst from the liquid phase, this latter being directed towards a downstream treatment zone to result in the production of fuels, essentially gasoline, jet fuel and gas oil.

The phase containing the major portion of the solid particles (termed concentrated liquid) is generally recycled to the synthesis reactor.

In general, the "slurry" medium in a Fischer-Tropsch process may be charged with catalyst particles to concentrations in the range 10% to 60% by weight, preferably in the range 20% to 45% by weight.

The solid particle separation devices can recycle to the reactor a suspension the solid particle concentration of which is increased by about 10%, relative value, with respect to the concentration in the suspension to be treated.

Many of the devices used in the prior art are located inside the Fischer-Tropsch synthesis reactor itself.

Documents describing the devices located outside the synthesis reactor which may be cited include:

U.S. Pat. No. 5,770,629 which describes an external filtration zone which, however, is not based on the principle of decantation. The device of the present invention does not have any filtration elements;

WO-98/27181 describes a decanter provided with a tubular internal element which can define an annular recirculation zone used to recover clear liquid. The device of the present invention does not have a recirculation zone.

BRIEF DESCRIPTION OF THE DRAWING FIGURE

FIG. 1 is a diagrammatic view of a device in accordance with the present invention which shows the principal characteristics together.

From bottom to top, the first volume (SL) corresponds to the suspension concentrated in solid particles. The second volume (L) corresponds to the suspension comprising liquid and solid, less charged with solid particles, and the third volume (G) located above the second volume (L) corresponds to a zone essentially composed of gas.

BRIEF DESCRIPTION OF THE INVENTION

The present invention consists of a device allowing the separation of fine particles of solid with a diameter generally in the range 10 to 100 microns, dispersed in the form of a suspension in a liquid, said device comprising an upper portion which is cylindrical in shape with a ratio H/D in the range 2 to 6, and a lower conical portion having the same maximum diameter as the cylindrical portion, the cone angle being in the range 40° to 60°, said device further comprising:

a tube (Ta) for admitting the suspension in the form of an elbow, the horizontal portion of said elbow, with diameter (d1), penetrating into the interior of the upper portion of the device, and the vertical portion of said elbow, with diameter (d2), opening substantially at the level of the plane separating the upper portion and the lower portion of the device, the ratio of the diameters, d2/d1, being in the range 2 to 4, and the vertical portion of the admission tube (Ta) having a length (hb) equal to at least three times the diameter (d2) of the end of the outlet from said vertical portion;

an upper withdrawal tube (Ts) for clear liquid located at the top of the upper cylindrical portion;

a lower withdrawal tube (Ti) for solid particles located at the bottom of the lower conical portion.

The present invention also consists in a process for separating solid particles with a diameter in the range 10 to 100 microns dispersed in a liquid with a viscosity of more than 0.2 mPa·s using the device described above.

The invention is preferably applied to a Fischer-Tropsch synthesis process employing a Fischer-Tropsch synthesis reactor in slurry mode with a catalyst constituted by fine particles with a diameter in the range 10 to 100 microns in suspension in a liquid with a viscosity of more than 0.2 mPa·s, in which said process uses a device in accordance with the invention located externally of the synthesis reactor, and the particles extracted from said device via the lower tube (Ti) are recycled to the reactor by means of a pump.

DETAILED DESCRIPTION OF THE INVENTION

The device of the present invention can separate solid particles with a diameter in the range 10 to 100 microns dispersed in the form of a suspension in a liquid with a viscosity of more than 0.2 mPa·s.

Said device consists of an upper portion which is cylindrical in shape with a ratio H/D in the range 2 to 6, and preferably in the range 2.5 to 5, and a lower conical portion with the same maximum diameter as the cylindrical portion, the cone angle ($\alpha$) being in the range 40° to 60°, preferably in the range 45° to 55°.

In general, the diameter of the decanter according to the invention is in the range 1 to 10 meters, preferably in the range 2 to 8 meters, and more preferably in the range 3 to 7 meters.

In the remainder of the text, the terms "upper portion" or "cylindrical portion" on the one hand, and "lower portion" or "conical portion" on the other hand will be used interchangeably.

Said device also comprises:

a tube (Ta) for admitting the suspension in the form of an elbow, the horizontal portion of said elbow, with diameter (d1), penetrating into the interior of the upper portion of the device, and the vertical portion of said elbow, with diameter (d2), opening substantially at the level of the plane separating the upper portion and the lower portion of the device, the ratio of the diameters, d2/d1, being in the range 2 to 4;

an upper withdrawal tube (Ts) for clear liquid located at the top of the upper cylindrical portion;

a lower withdrawal tube (Ti) for solid particles located at the bottom of the lower conical portion.

The term "substantially" means that the opening from the vertical portion of the admission tube (Ta) is at the level of the plane separating the upper portion and the lower portion of the device, plus or minus 0.5 meter.

The admission tube (Ta) for the suspension has a vertical portion (hb) the length of which is equal to at least 3 times the diameter (d2) of the outlet end of said vertical portion.

In accordance with a preferred characteristic of the device of the invention, the withdrawal tube (Ts) for clear liquid has a vertical portion which is substantially centred on the axis of symmetry of the decanter and immersed to a depth in the range 0.2 to 1 meter below the level of said clear liquid ($H_L$) and preferably at a depth in the range 0.3 to 0.7 meters below said level ($H_L$) for values of H which are preferably in the range 4 to 40 meters, and more preferably in the range 6 to 30 meters.

In accordance with a preferred characteristic of the device, it is provided with an internal baffle (B) fixed to the inner wall of the cylindrical portion of said device, and making an angle ($\beta$) with respect to the vertical which is substantially identical to the cone half angle ($\alpha$) of the lower portion of the device. The term "substantially" means a difference between angle ($\beta$) and angle ($\alpha$) of less than 10°.

In accordance with another preferred characteristic, the baffle (B) is fixed at a level which is substantially identical to the level at which the vertical portion of the admission tube (Ta) starts (moving from top to bottom).

The term "substantially" means a level corresponding to that of the start of the vertical portion of the admission tube (Ta), said level being in the range +0.3 m to −0.3 m with respect to said level (hb) of the vertical portion.

The height h1 of the baffle (B) is in the range 0.4 to 0.6 times the height of the vertical portion of the admission tube (Ta). Said vertical portion is denoted (hb) in FIG. 1.

The admission tube (Ta) penetrates into the interior of the cylindrical portion of the device in a manner which is substantially perpendicular to said cylindrical wall. The level of the horizontal portion of the admission tube (Ta) is more accurately the level of the horizontal axis of said tube, denoted (h) in FIG. 1.

The level of the liquid ($H_L$) in the device may be adjusted using any means which is known to the skilled person, such as a means acting on the flow rate of the exiting clear liquid (A), or on the flow rate of the exiting solid particles (5), or even on the flow rate of the suspension to be treated (E).

Preferably, said liquid level is selected so that the clear liquid withdrawal tube (Ts) is immersed to a depth in the range 0.3 to 0.7 meters below said liquid level ($H_L$).

The device of the present invention may be used in a process in which the flow rate of the liquid in the clear liquid withdrawal tube (Ts) is generally in the range 0.1 m/s to 0.3 m/s.

The device of the present invention may also be used in a process in which the velocity of the suspension in the lower solid particle withdrawal tube (Ti) is generally in the range 0.8 m/s to 3 m/s.

The device of the present invention may be used in a process for separating fine particles with a diameter in the range 10 to 100 microns in suspension in a liquid with a viscosity of more than 0.2 mPa·s, said process succeeding in delivering at least 99% by weight of particles entering with a diameter of more than 20 microns to the lower portion of said device.

The device of the present invention may be used in a process for separating fine particles with a diameter in the range 10 to 100 microns in suspension in a liquid with a viscosity of more than 0.2 mPa·s, said process having a suspension temperature in the range 180° C. to 250° C.

The invention also concerns a process for separating particles using the device of the present description.

The device of the present invention may be used in a process for separating fine particles with a diameter in the range 10 to 100 microns in suspension in a liquid with a viscosity of more than 0.2 mPa·s, said process producing a liquid concentrated in solid particles (principally located in the conical portion) with a concentration which is greater by at least 10%, relative value, than that of the suspension introduced into said device.

The device of the present invention may be used in a process, in which the level of the liquid ($H_L$) is automatically adjusted using a level controller (LC) by acting on the withdrawal flow rate of the clear liquid.

The invention thus also and preferably concerns a Fischer-Tropsch synthesis process employing a separate synthesis reactor in slurry mode with a catalyst constituted by fine particles with a diameter in the range 10 to 100 microns in suspension in a liquid with a viscosity of more than 0.2 mPa·s, in which said process uses a device (decanter) of the invention located externally of the synthesis reactor and the particles extracted from said device via the lower tube (Ti) are recycled to the reactor by means of a pump.

EXAMPLE

In Accordance with the Invention

A suspension was treated which was derived from a Fischer-Tropsch synthesis reactor and was constituted by catalyst particles, said particles being in suspension in a liquid with a density of 720 kg/m$^3$ and a viscosity of 0.7 mPa·s, under the following operating conditions: temperature 200° C. and pressure of 25 bars (1 bar=10$^5$ pascal).

The density of the suspension (liquid+particles) at the device inlet was: 1100 kg/m$^3$.

The flow rate of the suspension to be treated was 115 tonnes/hour.

The diameter of the particles was in the range 25 to 80 microns with a mean diameter of 55 microns. The device of the invention had the following dimensions:

Diameter (D): 5.5 m;
Height of cylindrical portion: 13.8 m;
Height of conical portion: 2.8 m;
Cone angle ($\alpha$): 45°;
Level for introduction of admission tube (h): 1.8 m;
Diameter of admission tube in its horizontal portion (d1): 0.15 m;
Diameter of admission tube in its vertical portion (d2): 0.38 m;
Diameter of clear liquid evacuation tube (d3): 0.20 m;
Diameter of concentrated suspension withdrawal tube (d4): 0.15 m;
Angle of inclination ($\beta$) of internal baffle: 50°;
Height of internal baffle ($h_1$): 0.75 m;
Height of vertical portion of admission tube (hb): 1.5 m;
Position of baffle: at height (hb) from start of vertical portion of the admission tube (Ta);

The clear liquid evacuation tube was immersed 0.5 m below the level of the gas-liquid interface.

The inlet concentration of solid particles in the suspension was in the range 20% to 30% by weight and it was shown, using a numerical simulation which reproduced the geometry of the decanter as defined above in fine detail (and in particular the geometry of the admission tube (Ta) in the form of an elbow), that the concentration in the liquid withdrawn via the tube (Ti) was increased by 7%, relative value, with respect to the concentration of the suspension at the inlet.

Further, a measurement of the grain size of a sample of the suspension recovered from the outlet tube (Ti) showed that the proportion of the particles having a diameter of more than 20 microns was 99.8% by weight (as opposed to 98% in the entering suspension).

The invention claimed is:

1. A device allowing the separation of particles of solid with a diameter in the range of 10 to 100 microns, dispersed in the form of a suspension in a liquid, said device comprising an upper portion which is cylindrical in shape with a ratio H/D in the range of 2 to 6, and a lower conical portion having the same maximum diameter as the cylindrical portion, the cone angle being in the range of 40° to 60°, said device further comprising:
    a tube (Ta) for admitting the suspension in the form of an elbow, the horizontal portion of said elbow, with diameter (d1), penetrating into the interior of the upper portion of the device, and the vertical portion of said elbow, with diameter (d2), opening substantially at the level of the plane separating the upper portion and the lower portion of the device, the ratio of the diameters, d2/d1, being in the range of 2 to 4, and the vertical portion of the admission tube (Ta) having a length (hb) equal to at least three times the diameter (d2) of the end of the outlet from said vertical portion;
    an upper withdrawal tube (Ts) for clear liquid located at the top of the upper cylindrical portion;
    a lower withdrawal tube (Ti) for solid particles located at the bottom of the lower conical portion; and
    an internal baffle (B) making an angle ($\beta$) with respect to the vertical, which is substantially equal to the cone half angle ($\alpha$) of the lower portion of the device, is fixed to the internal wall of the cylindrical portion of the device, at a level substantially identical to the level of the start of the vertical portion of the admission tube (Ta), the height of said baffle (B) being in the range of 0.4 to 0.6 times the height of the vertical portion of the admission tube (hb).

2. A device allowing separation of solid particles according to claim 1, in which the diameter D is in the range of 1 to 10 meters.

3. A separation device according to claim 1, in which the clear liquid withdrawal tube (Ts) has a vertical substantially centered portion which is immersed to a depth in the range of 0.2 to 1 meter below the level of said clear liquid ($H_L$).

4. A separation device according to claim 1, in which an internal baffle (B) making an angle ($\beta$) with respect to the vertical, which is substantially equal to the cone half angle ($\alpha$) of the lower portion of the device, is fixed to the internal wall of the cylindrical portion of the device, at a level substantially identical to the level of the start of the vertical portion of the admission tube (Ta), the height of said baffle (B) being 0.5 times the height of the vertical portion of the admission tube (hb).

5. A process for separating solid particles with a diameter in the range of 10 to 100 microns dispersed in a liquid with a viscosity of more than 0.2 mPa·s, wherein said process is performed in the device according to claim 1.

6. A separation process according to claim 5, in which the level of the liquid ($H_L$) is automatically adjusted by a level controller by acting on the withdrawal flow rate of the clear liquid.

7. A separation process according to claim 5, in which the temperature of the suspension introduced into the device is in the range of 180° C. to 250° C.

8. A separation process according to claim 5, in which the liquid concentrated in solid particles located in the lower conical portion has a concentration which is at least 10% higher than the concentration of the suspension introduced into the device.

9. A separation process according to claim 5, in which the flow rate of the liquid in the clear liquid withdrawal tube (Ts) is in the range of 0.1 to 0.3 m/s.

10. A separation process according to claim 5, in which the flow rate of the suspension in the lower solid particles withdrawal tube (Ti) is in the range of 0.8 m/s to 3 m/s.

11. A Fischer-Tropsch synthesis process employing a Fischer-Tropsch synthesis reactor in slurry mode with a catalyst constituted by fine particles with a diameter in the range of 10 to 100 microns in suspension in a liquid with a viscosity of more than 0.2 mPa·s, said process employing a device according to claim 1 located externally to the synthesis reactor, and the particles extracted from said device via the lower tubular (Ti) being recycled to the Fischer-Tropsch synthesis reactor by a pump.

12. A device allowing separation of solid particles according to claim 1, in which the diameter D is in the range of 2 to 8 meters.

13. A separation device according to claim 1, in which the clear liquid withdrawal tube (Ts) has a vertical substantially centered portion which is immersed to a depth in the range of 0.3 to 0.7 meter below the level of said clear liquid ($H_L$).

14. A separation device according to claim 1, which comprises a level controller which is capable of automatically adjusting the level of a liquid ($H_L$) in said device by acting on the withdrawal flow rate of a clear liquid.

15. A separation device according to claim 1, in which an internal baffle (B) making an angle ($\beta$) with respect to the vertical, which is substantially equal to the cone half angle ($\alpha$) of the lower portion of the device, is fixed to the internal wall of the cylindrical portion of the device, at a level substantially identical to the level of the start of the vertical portion of the admission tube (Ta), the height of said baffle (B) being 0.4 times the height of the vertical portion of the admission tube (hb).

16. A separation device according to claim 1, in which an internal baffle (B) making an angle ($\beta$) with respect to the vertical, which is substantially equal to the cone half angle ($\alpha$) of the lower portion of the device, is fixed to the internal wall of the cylindrical portion of the device, at a level substantially identical to the level of the start of the vertical portion of the admission tube (Ta), the height of said baffle (B) being 0.4 times the height of the vertical portion of the admission tube (hb).

* * * * *

UNITED STATES PATENT AND TRADEMARK OFFICE
CERTIFICATE OF CORRECTION

PATENT NO.       : 8,603,343 B2  
APPLICATION NO.  : 12/738356  
DATED            : December 10, 2013  
INVENTOR(S)      : Viguie et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 826 days.

Signed and Sealed this
Twenty-second Day of September, 2015

Michelle K. Lee
*Director of the United States Patent and Trademark Office*